(12) United States Patent
Ding et al.

(10) Patent No.: US 10,901,507 B2
(45) Date of Patent: Jan. 26, 2021

(54) BIOELECTRICITY-BASED CONTROL METHOD AND APPARATUS, AND BIOELECTRICITY-BASED CONTROLLER

(71) Applicant: Huawei Technologies Co., Ltd., Shenzhen (CN)

(72) Inventors: Qiang Ding, Shenzhen (CN); Can Zhang, Shenzhen (CN); Liyao Zhang, Beijing (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 101 days.

(21) Appl. No.: 15/908,179

(22) Filed: Feb. 28, 2018

(65) Prior Publication Data

US 2018/0188809 A1   Jul. 5, 2018

Related U.S. Application Data

(63) Continuation of application No. PCT/CN2016/079325, filed on Apr. 14, 2016.

(30) Foreign Application Priority Data

Aug. 28, 2015   (CN) .......................... 2015 1 0543246

(51) Int. Cl.
*G06F 3/01* (2006.01)
*A61B 5/0488* (2006.01)

(52) U.S. Cl.
CPC ............ *G06F 3/015* (2013.01); *A61B 5/0488* (2013.01); *G06F 3/017* (2013.01)

(58) Field of Classification Search
None
See application file for complete search history.

(56) References Cited

U.S. PATENT DOCUMENTS

| 8,447,704 B2 | 5/2013 | Tan et al. |
| 8,784,271 B2 | 7/2014 | Brumback et al. |

(Continued)

FOREIGN PATENT DOCUMENTS

| CN | 101482773 A | 7/2009 |
| CN | 103246836 A | 8/2013 |

(Continued)

*Primary Examiner* — Stephen T. Reed
(74) *Attorney, Agent, or Firm* — Leydig, Voit & Mayer, Ltd.

(57) ABSTRACT

The present invention relates to the field of natural human-computer interaction technologies, and discloses a bioelectricity-based control method and apparatus, and a bioelectricity-based controller, so as to improve naturalness of human-computer interaction. The method is as follows: performing characteristic extraction on a collected surface electromyography signal generated when a user performs a finger press operation, so as to obtain characteristic information; determining, according to a pre-created finger type recognition template, a finger type that is used to perform the finger press operation and that is corresponding to the obtained characteristic information; and mapping the determined finger type used to perform the finger press operation to a corresponding first instruction, and controlling a controlled device according to the first instruction. In this way, the controlled device may be controlled in a more harmonious and natural human-computer interaction manner.

10 Claims, 5 Drawing Sheets

(56) References Cited

U.S. PATENT DOCUMENTS

| | | | |
|---|---|---|---|
| 2009/0327171 A1* | 12/2009 | Tan | G06F 3/015 |
| | | | 706/12 |
| 2010/0302137 A1* | 12/2010 | Benko | G06F 3/005 |
| | | | 345/156 |
| 2010/0315266 A1 | 12/2010 | Gunawardana et al. | |
| 2012/0249417 A1 | 10/2012 | Cho et al. | |
| 2012/0303851 A1 | 11/2012 | Tseng et al. | |
| 2013/0196590 A1 | 8/2013 | Fyke et al. | |
| 2014/0106710 A1 | 4/2014 | Rodriguez | |
| 2015/0072619 A1* | 3/2015 | Abdurrahman | G06F 21/74 |
| | | | 455/41.2 |

FOREIGN PATENT DOCUMENTS

| | | |
|---|---|---|
| CN | 103309584 A | 9/2013 |
| CN | 203224838 U | 10/2013 |
| CN | 103442129 A | 12/2013 |
| CN | 103823551 A | 5/2014 |
| CN | 104461365 A | 3/2015 |
| CN | 104536558 A | 4/2015 |
| CN | 104571517 A | 4/2015 |
| CN | 104714645 A | 6/2015 |

\* cited by examiner

BIOELECTRICITY-BASED CONTROL METHOD AND APPARATUS, AND BIOELECTRICITY-BASED CONTROLLER

CROSS-REFERENCE TO RELATED APPLICATIONS

This application is a continuation of International Application No. PCT/CN2016/079325, filed on Apr. 14, 2016, which claims priority to Chinese Patent Application No. 201510543246.8, filed on Aug. 28, 2015. The disclosures of the aforementioned applications are hereby incorporated by reference in their entireties.

TECHNICAL FIELD

The present invention relates to the field of natural human-computer interaction technologies, and in particular, to a bioelectricity-based control method and apparatus, and a bioelectricity-based controller.

BACKGROUND

With development of Internet technologies, a human-computer interaction manner is in constant progress. Currently, most human-computer interaction manners widely used are based on a keyboard and a touchscreen. However, with growing popularity of wearable devices, a conventional human-computer interaction manner based on a keyboard and a touchscreen faces a challenge. The human-computer interaction manner based on a keyboard and a touchscreen needs to rely on a specific input device and operation interface. However, a wearable device is generally compact, and most wearable devices have no operation interface. Therefore, it is extremely unnatural and inconvenient to control a wearable device in the conventional human-computer interaction manner.

Currently, a more harmonious and natural human-computer interaction manner attracts extensive attention from all circles such as the academic and industrial circles. This human-computer interaction manner is more capable of performing interaction by means of a human intention, has a higher intention perception capability, and emphasizes more on naturalness of an interaction manner and harmony of a human-computer relationship. A physical human-computer interaction interface insists on "returning to the real world" and combines the real world and a digital world organically.

In conclusion, in the prior art, it is inconvenient and unnatural to control a wearable device based on the conventional human-computer interaction manner, and this is far away from a real natural environment. As a result, the wearable device cannot be controlled in a more natural and friendly interaction manner.

SUMMARY

Embodiments of the present invention provide a bioelectricity-based control method and apparatus, and a bioelectricity-based controller, so as to resolve a prior-art problem that it is inconvenient and unnatural to control a wearable device in a conventional human-computer interaction manner.

Specific technical solutions provided in the embodiments of the present invention are as follows.

According to a first aspect, a bioelectricity-based control method is provided, including:

collecting a surface electromyography signal generated when a user performs a finger press operation;

performing characteristic extraction on the collected surface electromyography signal, so as to obtain characteristic information;

determining, according to a pre-created finger type recognition template, a finger type that is used to perform the finger press operation and that is corresponding to the obtained characteristic information, where the finger type recognition template includes a correspondence between each finger type and characteristic information of a surface electromyography signal corresponding to each finger type when a finger press operation is performed; and mapping the determined finger type used to perform the finger press operation to a corresponding first instruction, and controlling a controlled device according to the first instruction.

With reference to the first aspect, in a first possible implementation of the first aspect, before the performing characteristic extraction on the collected surface electromyography signal, the method further includes:

performing preprocessing and sampling processing on the collected surface electromyography signal, where the preprocessing includes signal amplification and interference suppression.

With reference to the first aspect or the first possible implementation of the first aspect, in a second possible implementation of the first aspect, after the determining a finger type used to perform the finger press operation, the method further includes:

determining, based on an amplitude of the collected surface electromyography signal and a pre-created correlation function corresponding to a finger type, pressing force corresponding to the finger press operation, where the correlation function corresponding to a finger type includes a function relationship between pressing force and an amplitude of a surface electromyography signal generated when a finger press operation is performed based on each finger type; and mapping the determined finger type together with the pressing force corresponding to the finger press operation to a corresponding second instruction, and controlling the controlled device according to the second instruction.

With reference to the second possible implementation of the first aspect, in a third possible implementation of the first aspect, the surface electromyography signal includes multiple channel sub-signals; and the amplitude of the surface electromyography signal is determined in the following manner:

performing cumulative average calculation on signal amplitudes of all channel sub-signals included in the collected surface electromyography signal, so as to obtain an average signal amplitude of the surface electromyography signal, and using the average signal amplitude as the amplitude of the surface electromyography signal.

According to a second aspect, a bioelectricity-based control apparatus is provided, including:

a collection unit, configured to collect a surface electromyography signal generated when a user performs a finger press operation;

a characteristic extraction unit, configured to perform characteristic extraction on the surface electromyography signal collected by the collection unit, so as to obtain characteristic information;

a determining unit, configured to determine, according to a pre-created finger type recognition template, a finger type that is used to perform the finger press operation and that is corresponding to the characteristic information obtained by the characteristic extraction unit, where the finger type recognition template includes a correspondence between each finger type and characteristic information of a surface electromyography signal corresponding to each finger type when a finger press operation is performed; and a control unit, configured to map the finger type that is used to perform the finger press operation and that is determined by the determining unit to a corresponding first instruction, and control a controlled device according to the first instruction.

With reference to the second aspect, in a first possible implementation of the second aspect, the apparatus further includes:

a preparing unit, configured to: before the characteristic extraction unit performs the characteristic extraction on the surface electromyography signal collected by the collection unit, perform preprocessing and sampling processing on the collected surface electromyography signal, where the preprocessing includes signal amplification and interference suppression.

With reference to the second aspect or the first possible implementation of the second aspect, in a second possible implementation of the second aspect, the determining unit is further configured to:

determine, based on an amplitude of the surface electromyography signal collected by the collection unit and a pre-created correlation function corresponding to a finger type, pressing force corresponding to the finger press operation, where the correlation function corresponding to a finger type includes a function relationship between pressing force and an amplitude of a surface electromyography signal generated when a finger press operation is performed based on each finger type; and the control unit is further configured to map the finger type determined by the determining unit together with the pressing force corresponding to the finger press operation to a corresponding second instruction, and control the controlled device according to the second instruction.

With reference to the second possible implementation of the second aspect, in a third possible implementation of the second aspect, the surface electromyography signal includes multiple channel sub-signals; and the determining unit is specifically configured to determine the amplitude of the surface electromyography signal in the following manner:

performing cumulative average calculation on signal amplitudes of all channel sub-signals included in the collected surface electromyography signal, so as to obtain an average signal amplitude of the surface electromyography signal, and using the average signal amplitude as the amplitude of the surface electromyography signal.

According to a third aspect, a bioelectricity-based controller is provided, including a sensor, a processor, and a transceiver, where the sensor is configured to be in contact with an arm muscle surface of a user, so as to collect a surface electromyography signal generated when the user performs a finger press operation;

the processor is configured to invoke a set of program code, and perform the following operations according to the program code: performing characteristic extraction on the surface electromyography signal collected by the sensor, so as to obtain characteristic information; determining, according to a pre-created finger type recognition template, a finger type that is used to perform the finger press operation and that is corresponding to the obtained characteristic information; and mapping the determined finger type used to perform the finger press operation to a corresponding first instruction, where the first instruction is used to control a controlled device, and the finger type recognition template includes a correspondence between each finger type and characteristic information of a surface electromyography signal corresponding to each finger type when a finger press operation is performed; and the transceiver is configured to send the first instruction obtained by the processor to the controlled device.

With reference to the third aspect, in a first possible implementation of the third aspect, the bioelectricity-based controller further includes:

a memory, configured to store the program code executed by the processor.

With reference to the third aspect or the first possible implementation of the third aspect, in a second possible implementation of the third aspect, the processor is further configured to:

before performing the characteristic extraction on the collected surface electromyography signal, perform preprocessing and sampling processing on the collected surface electromyography signal, where the preprocessing includes signal amplification and interference suppression.

With reference to any one of the third aspect, or the first to the second possible implementations of the third aspect, in a third possible implementation of the third aspect, the processor is further configured to:

determine, based on an amplitude of the collected surface electromyography signal and a pre-created correlation function corresponding to a finger type, pressing force corresponding to the finger press operation, where the correlation function corresponding to a finger type includes a function relationship between pressing force and an amplitude of a surface electromyography signal generated when a finger press operation is performed based on each finger type; and map the determined finger type together with the pressing force corresponding to the finger press operation to a corresponding second instruction, where the second instruction is used to control the controlled device.

With reference to the third possible implementation of the third aspect, in a fourth possible implementation of the third aspect, the surface electromyography signal includes multiple channel sub-signals; and the processor is specifically configured to determine the amplitude of the surface electromyography signal in the following manner:

performing cumulative average calculation on signal amplitudes of all channel sub-signals included in the collected surface electromyography signal, so as to obtain an average signal amplitude of the surface electromyography signal, and using the average signal amplitude as the amplitude of the surface electromyography signal.

In the embodiments of the present invention, a bioelectricity-based control apparatus collects a surface electromyography signal generated when a user performs a finger press operation, and performs characteristic extraction on the collected surface electromyography signal, so as to obtain characteristic information; determines, according to a pre-created finger type recognition template, a finger type that is used to perform the finger press operation and that is corresponding to the obtained characteristic information;

and maps the determined finger type used to perform the finger press operation to a corresponding first instruction, and controls a controlled device according to the first instruction. In this way, a controlled device such as a wearable device can be controlled by simply performing a press operation on any physical interface, without requiring a specific input device or operation interface. The operation is convenient and is not affected by environmental factors such as time, space, and location. In addition, a control process is close to a real natural environment, so that the controlled device is controlled in a more harmonious and natural human-computer interaction manner.

DESCRIPTION OF EMBODIMENTS

To make the objectives, technical solutions, and advantages of the present invention clearer, the following further describes the present invention in detail with reference to the accompanying drawings. Apparently, the described embodiments are merely a part rather than all of the embodiments of the present invention. All other embodiments obtained by persons of ordinary skill in the art based on the embodiments of the present invention without creative efforts shall fall within the protection scope of the present invention.

A bioelectricity-based control method and apparatus, and a bioelectricity-based controller are designed in embodiments of the present invention. When a user performs a finger press operation, a corresponding muscle group generates a surface electromyography signal because of tension and deformation. A finger type used to perform the finger press operation is recognized by collecting, processing, and analyzing the generated surface electromyography signal. The recognized finger type is mapped to a corresponding instruction, and a controlled device is controlled by using the instruction.

The controlled device involved in the embodiments of the present invention may include any electronic device that can receive a wired or wireless signal. Preferably, the controlled device is a wearable device, such as a smart watch, a smart band, a pair of smart glasses, or a pair of smart sports shoes.

With reference to specific embodiments, the bioelectricity-based control method and apparatus, and the bioelectricity-based controller that are provided in the embodiments of the present invention are described below in detail in the present invention.

Embodiment 1

Figure 1:
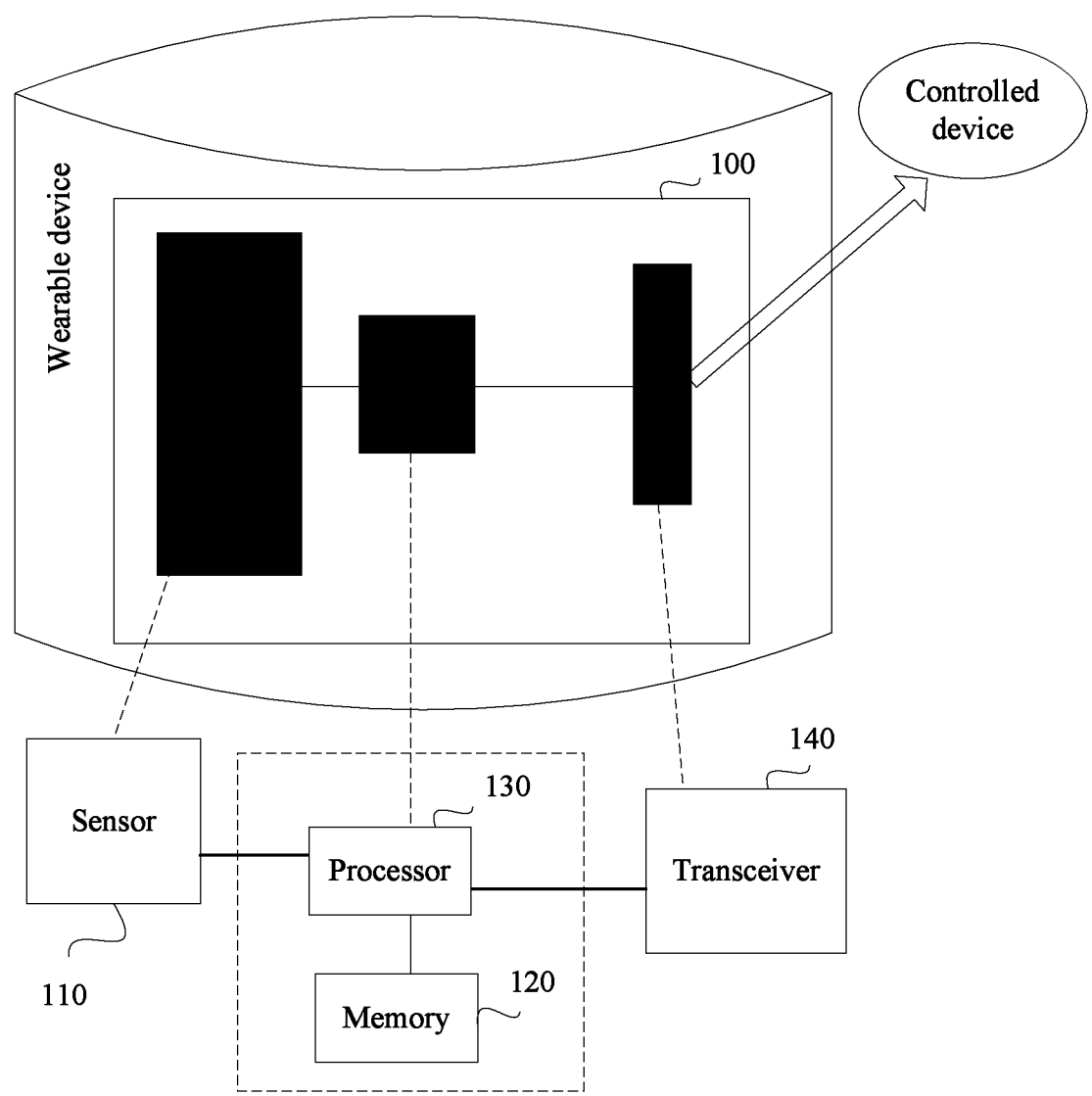
FIG. 1 is a structural diagram of a bioelectricity-based controller according to Embodiment 1 of the present invention.

Embodiment 1 of the present invention provides a bioelectricity-based controller (hereinafter referred to as a controller) 100. The controller 100 is configured to perform a method procedure subsequently involved in Embodiment 2. FIG. 1 is a schematic diagram of composition of the controller 100 according to this embodiment of the present invention. As shown in FIG. 1, the controller 100 includes a sensor 110, a processor 130, and a transceiver 140.

The sensor 110 is configured to be connected to an arm muscle surface of a user, so as to collect a surface electromyography signal generated when the user performs a finger press operation.

The processor 130 is configured to invoke a set of program code, and perform the following operations according to the program code: performing characteristic extraction on the surface electromyography signal collected by the sensor 110, so as to obtain characteristic information; determining, according to a pre-created finger type recognition template, a finger type that is used to perform the finger press operation and that is corresponding to the obtained characteristic information; and mapping the determined finger type used to perform the finger press operation to a corresponding first instruction, where the first instruction is used to control a controlled device.

The finger type recognition template includes a correspondence between each finger type and characteristic information of a surface electromyography signal corresponding to each finger type when a finger press operation is performed.

The transceiver 140 is configured to send the first instruction obtained by the processor 130 to the controlled device.

Preferably, the finger press operation is an operation of pressing any physical interface by using a finger, for example, an operation of pressing a desk by using a finger, an operation of pressing a key in a pocket by using a finger, or an operation of holding a cup by using a hand. In this way, a human-computer interaction manner provided in this embodiment of the present invention is more natural.

The controller 100 in Embodiment 1 of the present invention is disposed in a wearable device in a manner such as a chip. A manufacturing material of the wearable device is not limited. The wearable device is disposed around an arm of a user, and is closely attached to an arm muscle surface of the user. The sensor 110 needs to be disposed on an inner side of the wearable device, so as to be in contact with the arm muscle surface and collect a surface electromyography signal. For example, the wearable device may be a wrist strap. Because the surface electromyography signal is a weak biological signal, the wrist strap is closely attached to the arm muscle surface of the user, so that the sensor 110 in the controller 100 may effectively collect a surface electromyography signal generated when the user performs finger pressing.

With reference to Embodiment 1, in a first possible implementation, the controller 100 further includes a memory 120. The memory 120 is configured to store the program code executed by the processor 130.

With reference to Embodiment 1 or the first possible implementation, in a second possible implementation, the processor 130 is further configured to:

before performing the characteristic extraction on the collected surface electromyography signal, perform preprocessing and sampling processing on the collected surface electromyography signal, where the preprocessing includes signal amplification and interference suppression.

With reference to any one of Embodiment 1, or the first to the second possible implementations, in a third possible implementation, the processor 130 is further configured to:

determine, based on an amplitude of the collected surface electromyography signal and a pre-created correlation function corresponding to a finger type, pressing force corresponding to the finger press operation, where the correlation function corresponding to a finger type includes a function relationship between pressing force and an amplitude of a surface electromyography signal generated when a finger press operation is performed based on each finger type; and map the determined finger type together with the pressing force corresponding to the finger press operation to a corresponding second instruction, where the second instruction is used to control the controlled device.

With reference to the third possible implementation of Embodiment 1, in a fourth possible implementation, the surface electromyography signal includes multiple channel sub-signals.

The processor 130 is specifically configured to determine the amplitude of the surface electromyography signal in the following manner:

performing cumulative average calculation on signal amplitudes of all channel sub-signals included in the collected surface electromyography signal, so as to obtain an average signal amplitude of the surface electromyography signal, and using the average signal amplitude as the amplitude of the surface electromyography signal.

In Embodiment 1 of the present invention, by means of a controller closely attached to an arm muscle surface of a user, a surface electromyography signal may be collected when the user performs a finger press operation. The surface electromyography signal is processed and analyzed and is mapped to an instruction, so as to control a controlled device. In this way, a controlled device such as a wearable device can be controlled by simply performing a press operation on any physical interface, without requiring a specific input device or operation interface. The operation is convenient and is not affected by environmental factors such as time, space, and location. In addition, a control process is close to a real natural environment, so that the controlled device is controlled in a more harmonious and natural human-computer interaction manner.

Embodiment 2

Figure 2:
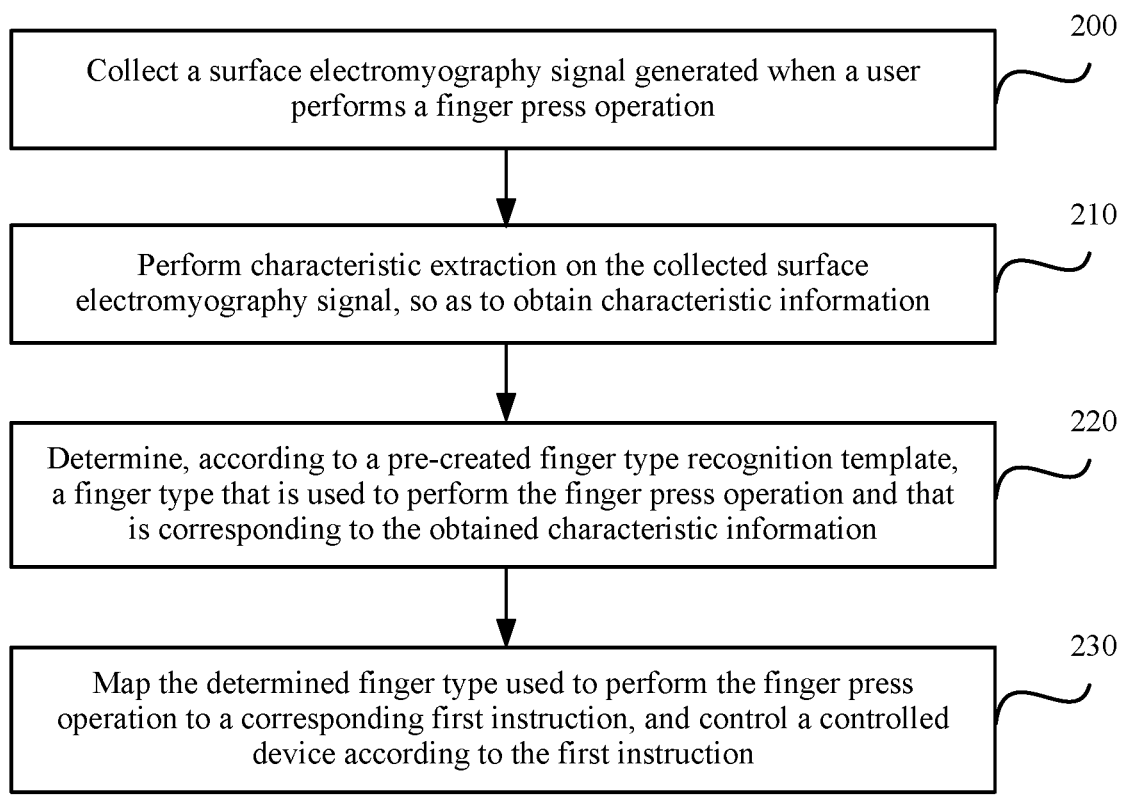
FIG. 2 is an implementation flowchart of a bioelectricity-based control method according to Embodiment 2 of the present invention.

Based on the bioelectricity-based controller provided in Embodiment 1, Embodiment 2 of the present invention provides a bioelectricity-based control method. FIG. 2 is an implementation flowchart of the bioelectricity-based control method provided in Embodiment 2 of the present invention. Embodiment 2 of the present invention is executed by the bioelectricity-based controller described in Embodiment 1. As shown in FIG. 2, the method includes the following steps.

Step 200: Collect a surface electromyography signal generated when a user performs a finger press operation.

In an actual application, when being in a to-be-controlled state, a controlled device may be controlled by a control apparatus. The to-be-controlled state means that the controlled device may receive an instruction to implement an application. For example, when being in a power-on state, the controlled device may receive an instruction to implement an application or an operation that can be performed in a standby state. For another example, when an application program is started on the controlled device, the controlled device may receive an instruction to implement an application or an operation that can be performed for the application program.

When the controlled device is in the to-be-controlled state, the user performs a finger press operation. Because an arm muscle of the user contracts, a surface electromyography signal is generated, and a control apparatus (such as a wrist strap) disposed around an arm of the user and closely attached to the arm of the user collects the generated surface electromyography signal. Because one action is generally completed by multiple muscles jointly, a controller is expected to collect multiple channels of surface electromyography signals at the same time. When a finger press operation is performed, the controller collects multiple channels of surface electromyography signals by using sensors disposed in different locations of the muscles.

The finger press operation performed by the user is an operation of pressing any interface by using a finger. For example, the finger press operation may be pressing a key in a pocket, a desk, a wall, another part of a body, or may be holding a cup. The any interface may be any medium that can make an arm muscle of the user generate a useful surface electromyography signal.

Step 210: Perform characteristic extraction on the collected surface electromyography signal, so as to obtain characteristic information.

Preferably, preprocessing and sampling processing are performed before the characteristic extraction is performed on the collected surface electromyography signal. The preprocessing includes signal amplification and interference suppression.

In step 200, the surface electromyography signal collected by the controller is an original surface electromyography signal. Because the surface electromyography signal is relatively weak, interference is inevitably introduced in a collection process. As a result, a useful surface electromyography signal is usually overwhelmed by noise. Therefore, the collected original surface electromyography signal needs to be preprocessed. A preprocessing process is not limited in this embodiment of the present invention. The preprocessing is mainly performing an operation such as amplification and interference suppression on the original surface electromyography signal. The interference suppression includes some filtering operations, such as industrial frequency filtering and high-pass filtering.

Afterward, sampling processing is performed on the preprocessed surface electromyography signal. The sampling processing may be sliding window processing.

Figure 3:
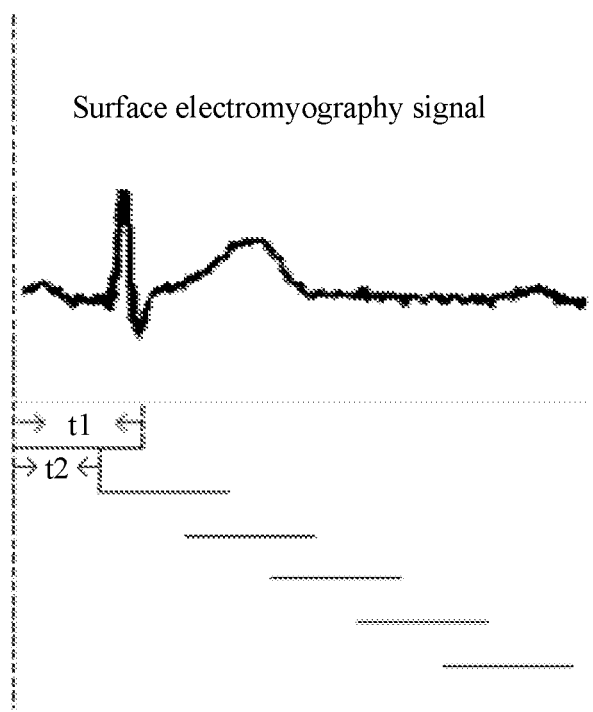
FIG. 3 is a schematic diagram of a sliding window processing process according to an embodiment of the present invention.

FIG. 3 shows a schematic diagram of a sliding window processing process according to an embodiment of the present invention.

A time segment t1 is used as a width of a sliding window, and a time segment t2 is used as a sampling interval for performing sampling on the preprocessed surface electromyography signal. In this way, the preprocessed surface electromyography signal is divided into multiple time windows, so as to form a window sequence.

Characteristic extraction is a basis for analyzing a surface electromyography signal. The characteristic extraction is performed on preprocessed surface electromyography signals of all time windows of all channels, so as to obtain characteristic information. There are many methods for performing the characteristic extraction. In this embodiment of the present invention, a time-domain analysis method is used as an example for description.

Preferably, the extracted characteristic information is a mean absolute value (represented by MAV) of the preprocessed surface electromyography signals of all time windows of all channels and first three coefficients a1, a2, and a3 of a four-order autoregressive (AutoRegressive, AR) model.

The mean absolute value MAV is defined as:

$$MAV = \frac{1}{N}\sum_{1}^{N}|X_i|,$$

where

N indicates a quantity of sampling points of the preprocessed surface electromyography signals of all time windows of all channels, and $X_i$ indicates an amplitude of a surface electromyography signal of an $i^{th}$ sampling point.

The AR model may be represented as follows:

$$x_k = -\sum_{i=1}^{N} a_i x_{k-i} + e_k,$$

where $X_k$ indicates a $k^{th}$ sampling point of the preprocessed surface electromyography signals of all time windows of all channels, $X_{k-1}$ indicates a $(k-1)^{th}$ sampling point, N=4, $a_i$ is an AR coefficient, i=1, 2, . . . , or N, and $e_k$ is residual white noise.

Step 220: Determine, according to a pre-created finger type recognition template, a finger type that is used to perform the finger press operation and that is corresponding to the obtained characteristic information.

The finger type recognition template includes a correspondence between each finger type and characteristic information of a surface electromyography signal corresponding to each finger type when a finger press operation is performed.

Specifically, before the controlled device is controlled by using the controller, the finger type recognition template is pre-created for the controlled device. A specific process is as follows:

(1) Collect a surface electromyography signal generated when the user performs key simulation on a physical interface by using any finger.

The user may determine pressing force according to a pressing habit of the user, and perform the key simulation on the physical interface by using the same or similar pressing force. In an actual application, the user also performs a press operation by using pressing force that is the same as or similar to the foregoing pressing force.

(2) Perform preprocessing such as signal amplification, industrial frequency filtering, and high-pass filtering on the collected surface electromyography signal.

(3) Perform sampling on the preprocessed surface electromyography signal, divide a surface electromyography signal of each channel into multiple time windows, and perform characteristic extraction on surface electromyography signals of all time windows of all channels, so as to obtain characteristic information.

The obtained characteristic information is a mean absolute value of the preprocessed surface electromyography signals of all time windows of all channels and first three coefficients a1, a2, and a3 of a four-order AR model.

A correspondence between each finger type and characteristic information of a surface electromyography signal corresponding to each finger type when a finger press operation is performed is used as the finger type recognition template.

The foregoing is the process of creating the finger type recognition template.

By means of linear discriminant analysis or another method, dimension reduction is performed on the characteristic information obtained in step 210. Then, according to the foregoing pre-created finger type recognition template, a support vector machine or another classifier is used to classify the characteristic information obtained by performing the dimension reduction, so as to recognize the finger type used to perform the finger press operation.

Step 230: Map the determined finger type used to perform the finger press operation to a corresponding first instruction, and control a controlled device according to the first instruction.

The first instruction is transferred to the external controlled device in a wired or wireless manner. The wireless manner includes but is not limited to any one or any combination of Wireless Fidelity (Wireless Fidelity, WiFi), Bluetooth, or ZigBee (ZigBee protocol).

Specifically, before the controlled device is controlled by using the controller, in addition to pre-creating the finger type recognition template for the controlled device, a mapping relationship between each finger type and a corresponding instruction needs to be established, so as to control the controlled device by using the instruction.

For example, the controlled device is a smart watch, an instruction to which a forefinger of a right hand is mapped is enabling a WeChat application, and an instruction to which a middle finger of the right hand is mapped is enabling a camera. When the smart watch is in the standby state, and when the user performs a finger press operation, the controller collects a surface electromyography signal generated on a surface of a muscle of a right arm of the user, and recognizes, by processing and analyzing the surface electromyography signal, that a finger used to perform the press operation is the forefinger of the right hand. The forefinger of the right hand is mapped to the instruction for enabling the WeChat application. Therefore, the smart watch is controlled to enable the WeChat application.

In addition, the foregoing method merely describes a process of collecting a surface electromyography signal generated by performing a press operation by using one finger, and mapping the surface electromyography signal to an instruction to control a controlled device. In an actual application, according to a requirement, before the controller is used to control the controlled device, a finger type recognition template when a physical interface is pressed by using at least any two finger types may be created, and a mapping relationship between the at least any two finger types and a corresponding instruction may be established. A surface electromyography signal generated when a press operation is performed by using the at least any two fingers is collected, and is mapped to an instruction to control the controlled device.

The foregoing embodiment describes a controlled device being controlled by mapping a finger type to an instruction. In this embodiment of the present invention, the controlled device may also be controlled by mapping a finger type together with pressing force to an instruction.

A specific process is as follows:

S1. After the finger type used to perform the finger press operation is determined in the foregoing step 220, determine, based on an amplitude of the preprocessed surface electromyography signal and a pre-created correlation function corresponding to a finger type, pressing force corresponding to the finger press operation.

The correlation function corresponding to a finger type includes a function relationship between pressing force and an amplitude of a surface electromyography signal generated when a finger press operation is performed based on each finger type.

The surface electromyography signal includes multiple channel sub-signals.

The amplitude of the surface electromyography signal is determined in the following manner:

performing cumulative average calculation on signal amplitudes of all channel sub-signals included in the collected (preferably, preprocessed) surface electromyography signal, so as to obtain an average signal amplitude of the surface electromyography signal, and using the average signal amplitude as the amplitude of the surface electromyography signal.

Specifically, before the controlled device is controlled by using the controller, the correlation function corresponding to a finger type further needs to be pre-created for the controlled device, and a mapping relationship between each finger type together with pressing force and a corresponding instruction need to be established, so as to control the controlled device by using the instruction.

A specific process of creating the correlation function corresponding to a finger type is as follows:

(1) Collect a surface electromyography signal generated when the user performs key simulation on a physical interface by using any finger with pressing force in ascending order.

(2) Perform preprocessing such as signal amplification, industrial frequency filtering, and high-pass filtering on the collected surface electromyography signal.

(3) Perform cumulative average calculation on amplitudes of preprocessed surface electromyography signals of all channels, and perform fitting analysis on the surface electromyography signal obtained by performing the cumulative average calculation, so as to obtain a function relationship between an amplitude of the foregoing surface electromyography signal generated when a finger press operation is performed by using any finger type and pressing force.

The foregoing is the process of creating the correlation function corresponding to a finger type.

Existing analysis indicates that there is a good linear relationship between a tension level of a muscle and an amplitude of a generated surface electromyography signal. The tension level of a muscle is positively correlated with pressing force of a finger press operation. Therefore, there is necessarily a good linear relationship between the pressing force and the amplitude of the surface electromyography signal.

Figure 4:
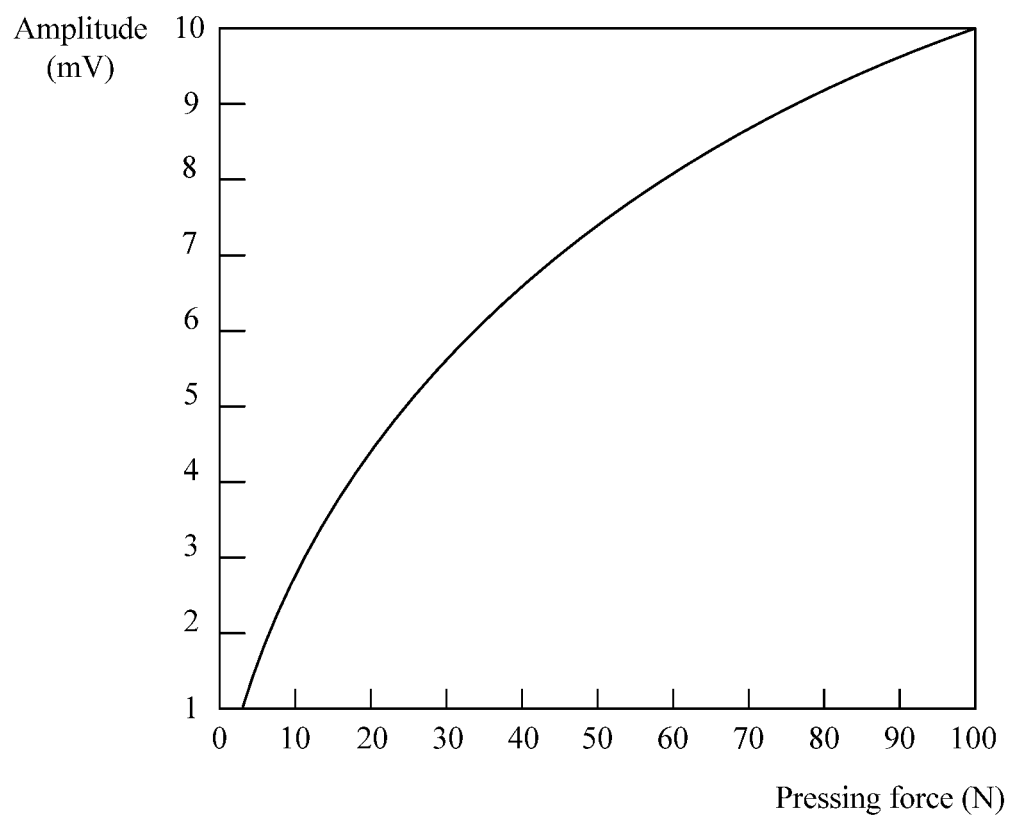
FIG. 4 is a diagram of an example of a relationship between an amplitude of a surface electromyography signal and pressing force according to an embodiment of the present invention.

In this embodiment of the present invention, it is discovered by performing fitting analysis on a large amount of data that there is a power function relationship between the amplitude of the surface electromyography signal and the pressing force. As shown in FIG. 4, FIG. 4 is a diagram of a relationship between an amplitude of a surface electromyography signal generated when a press operation is performed by using a middle finger of a right hand of a user and pressing force in an actual application according to an embodiment of the present invention.

S2. Map the finger type determined in step 230 together with the pressing force corresponding to the finger press operation to a corresponding second instruction, and control the controlled device according to the second instruction.

For example, the controlled device is a pair of smart glasses, a forefinger of a right hand is defined as left shifting of a cursor, a little finger of the right hand is defined as right shifting of the cursor, and pressing force is defined as a displacement of cursor shifting. When the pair of smart glasses is in a to-be-controlled state, a user performs a finger press operation. A controller collects a surface electromyography signal generated on a surface of a muscle of a right arm of the user, and recognizes, by processing and analyzing the surface electromyography signal, that a finger used to perform the press operation is the little finger of the right hand, and pressing force is obtained. The little finger of the right hand and the pressing force are mapped to a specific displacement of right shifting of the cursor.

In Embodiment 2 of the present invention, by means of a controller closely attached to an arm muscle surface of a user, a surface electromyography signal may be collected when the user performs a finger press operation. The surface electromyography signal is processed and analyzed and is mapped to an instruction, so as to control a controlled device. In this way, a controlled device such as a wearable device can be controlled by simply performing a press operation on any physical interface, without requiring a specific input device or operation interface. The operation is convenient and is not affected by environmental factors such as time, space, and location. In addition, a control process is close to a real natural environment, so that the controlled device is controlled in a more harmonious and natural human-computer interaction manner. A finger type together with pressing force is mapped to an instruction, so that an output instruction may be in a continuous state.

Embodiment 3

Figure 5:
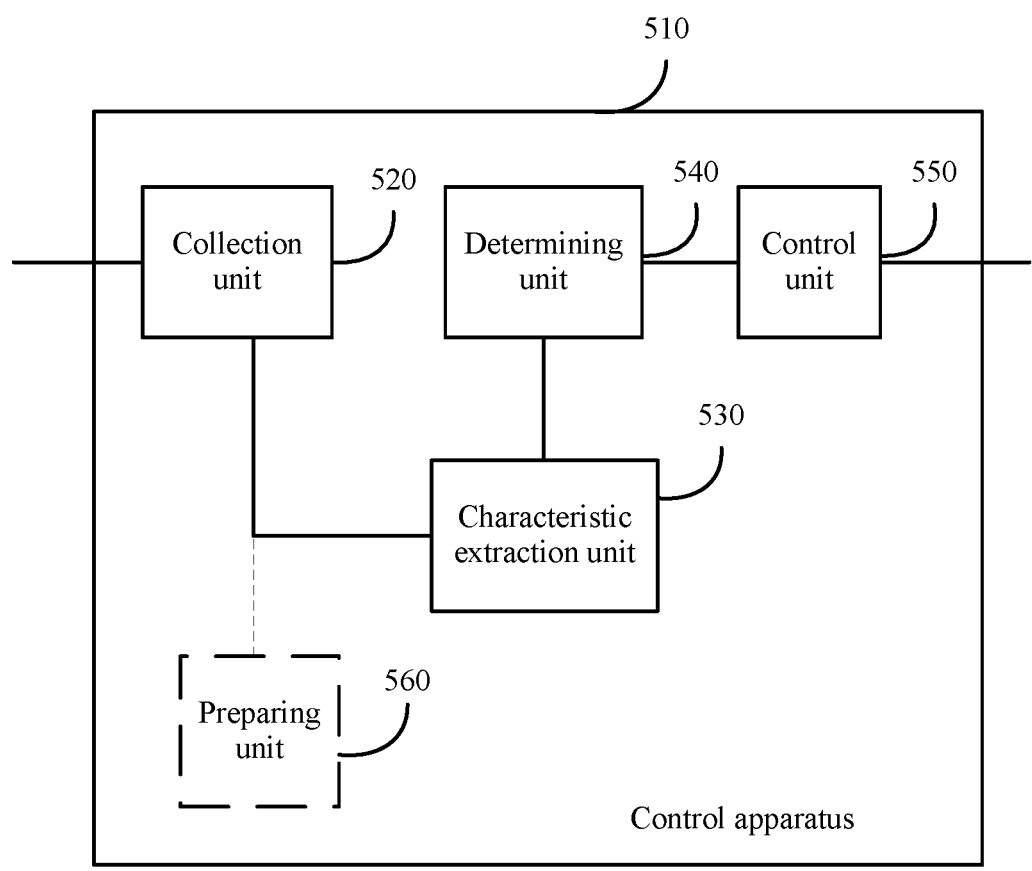
FIG. 5 is a structural diagram of a bioelectricity-based control apparatus according to Embodiment 3 of the present invention.

Based on Embodiment 1 and Embodiment 2, Embodiment 3 of the present invention provides a bioelectricity-based control apparatus (hereinafter referred to as a control apparatus) 510. FIG. 5 is a schematic diagram of composition of the control apparatus 510 provided in Embodiment 3 of the present invention. As shown in FIG. 5, the control apparatus 510 includes a collection unit 520, a characteristic extraction unit 530, a determining unit 540, and a control unit 550.

The collection unit 520 is configured to collect a surface electromyography signal generated when a user performs a finger press operation.

The finger press operation is an operation of pressing any interface by using a finger.

The characteristic extraction unit 530 is configured to perform characteristic extraction on the surface electromyography signal collected by the collection unit 520, so as to obtain characteristic information.

The determining unit 540 is configured to determine, according to a pre-created finger type recognition template, a finger type that is used to perform the finger press operation and that is corresponding to the characteristic information obtained by the characteristic extraction unit 530.

The finger type recognition template includes a correspondence between each finger type and characteristic information of a surface electromyography signal corresponding to each finger type when a finger press operation is performed.

The control unit 550 is configured to map the finger type that is used to perform the finger press operation and that is determined by the determining unit 540 to a corresponding first instruction, and control a controlled device according to the first instruction.

With reference to Embodiment 3, in a first possible implementation, the apparatus further includes:

a preparing unit 560, configured to: before the characteristic extraction unit 530 performs the characteristic extraction on the collected surface electromyography signal, perform preprocessing and sampling processing on the collected surface electromyography signal.

With reference to Embodiment 3 and the first possible implementation, in a second possible implementation, the determining unit 540 is further configured to:

determine, based on an amplitude of the surface electromyography signal collected by the collection unit 520 and a pre-created correlation function corresponding to a finger type, pressing force corresponding to the finger press operation.

The correlation function corresponding to a finger type includes a function relationship between pressing force and an amplitude of a surface electromyography signal generated when a finger press operation is performed based on each finger type.

The control unit 550 is further configured to map the finger type determined by the determining unit 540 together with the pressing force corresponding to the finger press operation to a corresponding second instruction, and control the controlled device according to the second instruction.

With reference to the third possible implementation, in a fourth possible implementation, the surface electromyography signal includes multiple channel sub-signals.

The determining unit 540 is specifically configured to determine the amplitude of the surface electromyography signal in the following manner:

performing cumulative average calculation on signal amplitudes of all channel sub-signals included in the collected surface electromyography signal, so as to obtain an average signal amplitude of the surface electromyography signal, and using the average signal amplitude as the amplitude of the surface electromyography signal.

In Embodiment 3 of the present invention, by means of a control apparatus closely attached to an arm muscle surface of a user, a surface electromyography signal may be collected when the user performs a finger press operation. The surface electromyography signal is processed and analyzed and is mapped to an instruction, so as to control a controlled device. In this way, a controlled device such as a wearable device can be controlled by simply performing a press operation on any physical interface, without requiring a specific input device or operation interface. The operation is convenient and is not affected by environmental factors such as time, space, and location. In addition, a control process is close to a real natural environment, so that the controlled device is controlled in a more harmonious and natural human-computer interaction manner.

Persons skilled in the art should understand that the embodiments of the present invention may be provided as a method, a system, or a computer program product. Therefore, the present invention may use a form of hardware only embodiments, software only embodiments, or embodiments with a combination of software and hardware. Moreover, the present invention may use a form of a computer program product that is implemented on one or more computer-usable storage media (including but not limited to a disk memory, a CD-ROM, an optical memory, and the like) that include computer-usable program code.

The present invention is described with reference to the flowcharts and/or block diagrams of the method, the device (system), and the computer program product according to the embodiments of the present invention. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner, so that the instructions stored in the computer readable memory generate an artifact that includes an instruction apparatus. The instruction apparatus implements a specific function in one or more processes in the flowcharts and/or in one or more blocks in the block diagrams.

These computer program instructions may be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Although some embodiments of the present invention have been described, persons skilled in the art can make changes and modifications to these embodiments once they learn the basic inventive concept. Therefore, the following claims are intended to be construed as to cover the preferred embodiments and all changes and modifications falling within the scope of the present invention.

Obviously, persons skilled in the art can make various modifications and variations to the embodiments of the present invention without departing from the spirit and scope of the embodiments of the present invention. The present invention is intended to cover these modifications and variations provided that they fall within the scope of protection defined by the following claims and their equivalent technologies.

What is claimed is:

1. A bioelectricity-based control method for controlling a device using a surface electromyography signal of a muscle of a user of the device, the method implemented in a controller including a sensor, a processor coupled to the sensor, and a transceiver coupled to the processor, the sensor configured to communicate with a muscle surface of the user, the method comprising:

collecting, by the sensor, the surface electromyography signal generated on the muscle surface when the user performs a finger press operation on a physical interface that is not specific to the device;

invoking, by the processor, a set of program code stored in a memory for execution by the processor to perform the following operations according to the program code:

performing preprocessing and sampling processing on the collected surface electromyography signal, wherein the preprocessing comprises signal amplification and interference suppression, and wherein the sampling processing is performed by sliding window processing, and wherein the interference suppression includes industrial frequency filtering and high-pass filtering;

performing characteristic extraction on the collected surface electromyography signal, so as to obtain characteristic information of the collected surface electromyography signal, wherein performing characteristic extraction comprises determining an amplitude of the collected surface electromyography signal;

determining, according to a pre-created finger type recognition template, at least two finger types that are used to perform the finger press operation and that correspond to the obtained characteristic information, wherein the finger type recognition template comprises a correspondence between the at least two finger types and characteristic information of respective surface electromyography signals corresponding to each of the at least two finger types when the finger press operation is performed; and mapping the determined finger type used to perform the finger press operation to a corresponding two finger types first instruction; and sending, by the transceiver, the two finger types first instruction to the device to facilitate controlling the device according to the first instruction.

2. The method according to claim 1, after the determining a finger type used to perform the finger press operation, further comprising:

determining, based on the amplitude of the collected surface electromyography signal and a pre-created correlation function corresponding to a finger type, a pressing force corresponding to the finger press operation, wherein the correlation function corresponding to a finger type comprises a function relationship between pressing force and an amplitude of a surface electromyography signal generated when a finger press operation is performed based on each finger type; and mapping the determined finger type together with the pressing force corresponding to the finger press operation to a corresponding second instruction, and controlling the controlled device according to the second instruction.

3. The method according to claim 2, wherein the surface electromyography signal comprises multiple channel sub-signals; and the amplitude of the surface electromyography signal is determined in the following manner:

performing cumulative average calculation on signal amplitudes of all channel sub-signals comprised in the collected surface electromyography signal, so as to obtain an average signal amplitude of the surface electromyography signal, and using the average signal amplitude as the amplitude of the surface electromyography signal.

4. A bioelectricity-based control apparatus for controlling a device using a surface electromyography signal of a muscle of a user of the device, the apparatus comprising:

a sensor configured to: communicate with a muscle surface of the user, and collect the surface electromyography signal generated on the muscle surface when the user performs a finger press operation on a physical interface that is not specific to the device;

a processor coupled to the sensor and configured to invoke a set of program code stored in a memory for execution by the processor to perform the following operations according to the program code:

performing preprocessing and sampling processing on the collected surface electromyography signal, wherein the preprocessing comprises signal amplification and interference suppression, and wherein the sampling processing is performed by sliding window processing, and wherein the interference suppression includes industrial frequency filtering and high-pass filtering;

performing characteristic extraction on the collected surface electromyography signal, so as to obtain characteristic information of the collected surface electromyography signal, wherein performing characteristic extraction comprises determining an amplitude of the collected surface electromyography signal;

determining, according to a pre-created finger type recognition template, at least two finger types that are used to perform the finger press operation and that correspond to the characteristic information of the collected surface electromyography signal, wherein the finger type recognition template comprises a correspondence between the at least two finger types and characteristic information of respective surface electromyography signals corresponding to each of the at least two finger types when the finger press operation is performed; and mapping the determined finger type used to perform the finger press operation to a corresponding two finger types first instruction; and a transceiver coupled to the processor and configured to send the two finger types first instruction to the device to facilitate controlling the device according to the first instruction.

5. The apparatus according to claim 4, wherein the processor is further configured to invoke the program code for execution by the processor for:

determining, based on the amplitude of the collected surface electromyography signal and a pre-created correlation function corresponding to a finger type, a pressing force corresponding to the finger press operation, wherein the correlation function corresponding to a finger type comprises a function relationship between pressing force and an amplitude of a surface electromyography signal generated when a finger press operation is performed based on each finger type; and mapping the determined finger type together with the pressing force corresponding to the finger press operation to a corresponding second instruction, and wherein the transceiver is further configured send the second instruction to the device to facilitate controlling the controlled device according to the second instruction.

6. The apparatus according to claim 5, wherein the surface electromyography signal comprises multiple channel sub-signals; and the processor is further configured to determine the amplitude of the surface electromyography signal in the following manner:

performing cumulative average calculation on signal amplitudes of all channel sub-signals comprised in the collected surface electromyography signal, so as to obtain an average signal amplitude of the surface electromyography signal, and using the average signal amplitude as the amplitude of the surface electromyography signal.

7. A bioelectricity-based controller, comprising a sensor, a processor, and a transceiver, wherein
the sensor is configured to be in communication with an arm muscle surface of a user, so as to collect a surface electromyography signal generated when the user performs a finger press operation on a physical interface that is not specific to a device;
the processor is coupled to the sensor and is configured to invoke a set of program code, and perform the following operations according to the program code: performing preprocessing and sampling processing on the collected surface electromyography signal, wherein the preprocessing comprises signal amplification and interference suppression, and wherein the sampling processing is performed by sliding window processing, and wherein the interference suppression includes industrial frequency filtering and high-pass filtering; performing characteristic extraction on the surface electromyography signal collected by the sensor, so as to obtain characteristic information of the collected surface electromyography signal; determining, according to a pre-created finger type recognition template, at least two finger types that are used to perform the finger press operation and that correspond to the obtained characteristic information; and mapping the determined finger type used to perform the finger press operation to a corresponding two finger types first instruction, wherein the finger type recognition template comprises a correspondence between each finger type and characteristic information of a surface electromyography signal corresponding to each finger type when a finger press operation is performed; and
the transceiver is coupled to the processor and is configured to send the two finger types first instruction obtained by the processor to the device to facilitate controlling the controlled device according to the first instruction.

8. The bioelectricity-based controller according to claim 7, further comprising:
a memory, configured to store the program code executed by the processor.

9. The bioelectricity-based controller according to claim 7, wherein the processor is further configured to:
determine, based on an amplitude of the collected surface electromyography signal and a pre-created correlation function corresponding to a finger type, pressing force corresponding to the finger press operation, wherein
the correlation function corresponding to a finger type comprises a function relationship between pressing force and an amplitude of a surface electromyography signal generated when a finger press operation is performed based on each finger type; and
map the determined finger type together with the pressing force corresponding to the finger press operation to a corresponding second instruction, wherein the transceiver is further configured to send the second instruction to the device to facilitate controlling the controlled device according to the second instruction.

10. The bioelectricity-based controller according to claim 9, wherein the surface electromyography signal comprises multiple channel sub-signals; and
the processor is specifically configured to determine the amplitude of the surface electromyography signal in the following manner:
performing cumulative average calculation on signal amplitudes of all channel sub-signals comprised in the collected surface electromyography signal, so as to obtain an average signal amplitude of the surface electromyography signal, and using the average signal amplitude as the amplitude of the surface electromyography signal.

* * * * *